US011726553B2

(12) United States Patent
Fortuna et al.

(10) Patent No.: US 11,726,553 B2
(45) Date of Patent: Aug. 15, 2023

(54) MOVEMENT-BASED NAVIGATION

(71) Applicant: SONY INTERACTIVE ENTERTAINMENT LLC, San Mateo, CA (US)

(72) Inventors: Ellana Fortuna, San Mateo, CA (US); Jennifer Sheldon, San Mateo, CA (US); Sarah Karp, San Mateo, CA (US)

(73) Assignee: SONY INTERACTIVE ENTERTAINMENT LLC, San Mateo, CA (US)

( * ) Notice: Subject to any disclaimer, the term of this patent is extended or adjusted under 35 U.S.C. 154(b) by 0 days.

(21) Appl. No.: 17/389,083

(22) Filed: Jul. 29, 2021

(65) Prior Publication Data
US 2023/0027393 A1   Jan. 26, 2023

Related U.S. Application Data

(60) Provisional application No. 63/223,816, filed on Jul. 20, 2021.

(51) Int. Cl.
| | | |
|---|---|---|
| *G06F 3/01* | (2006.01) | |
| *A61B 5/00* | (2006.01) | |
| *G06F 3/04815* | (2022.01) | |
| *G06T 13/40* | (2011.01) | |
| *G06T 19/00* | (2011.01) | |

(52) U.S. Cl.
CPC .............. *G06F 3/011* (2013.01); *G06F 3/017* (2013.01); *A61B 5/744* (2013.01); *G06F 3/04815* (2013.01); *G06T 13/40* (2013.01); *G06T 19/003* (2013.01); *G06T 19/006* (2013.01)

(58) Field of Classification Search
CPC ...... G06F 3/011; G06F 3/017; G06F 3/04815; A61B 5/744; G06T 13/40; G06T 19/003; G06T 19/006
See application file for complete search history.

(56) References Cited

U.S. PATENT DOCUMENTS

| | | |
|---|---|---|
| 3,430,530 A | 3/1969 | Grindinger |
| 7,071,914 B1 | 7/2006 | Marks |
| 7,559,841 B2 | 7/2009 | Hasimoto |
| | (Continued) | |

FOREIGN PATENT DOCUMENTS

| | | |
|---|---|---|
| CN | 115641421 | 1/2023 |
| CN | 115701082 | 2/2023 |
| | (Continued) | |

OTHER PUBLICATIONS

U.S. Appl. No. 17/403,242 Office Action dated Nov. 4, 2022.
(Continued)

*Primary Examiner* — Adam R. Giesy
(74) *Attorney, Agent, or Firm* — Polsinelli LLP

(57) ABSTRACT

One or more custom actions are stored in memory. Each of the custom actions is associated with a pattern of physical movement and a threshold. Physical movement data captured by a user device of the user is received and mapped to an identified one of the custom actions. When the physical movement data matches the associated pattern of physical movement within the associated threshold, it is determined that the user is authorized to access the identified custom action.

19 Claims, 5 Drawing Sheets

(56) References Cited

U.S. PATENT DOCUMENTS

| | | | |
|---|---|---|---|
| 8,284,157 | B2 | 10/2012 | Markovic et al. |
| 8,412,662 | B2 | 4/2013 | Ramic et al. |
| 8,427,508 | B2 | 4/2013 | Mattila et al. |
| 9,089,775 | B1 | 7/2015 | Daniel |
| 9,350,951 | B1 | 5/2016 | Rowe |
| 9,358,456 | B1 | 6/2016 | Challinor et al. |
| 10,701,316 | B1 | 6/2020 | Cheung et al. |
| 2002/0160823 | A1 | 10/2002 | Watabe et al. |
| 2004/0161132 | A1 | 8/2004 | Cohen et al. |
| 2008/0096657 | A1 | 4/2008 | Benoist |
| 2008/0234023 | A1 | 9/2008 | Mullahkhel et al. |
| 2009/0163262 | A1 | 6/2009 | Kang |
| 2009/0325705 | A1 | 12/2009 | Filer et al. |
| 2010/0050133 | A1 | 2/2010 | Nishihara et al. |
| 2010/0306712 | A1 | 12/2010 | Snook |
| 2011/0093820 | A1 | 4/2011 | Zhang |
| 2013/0172070 | A1 | 7/2013 | Kim et al. |
| 2013/0176437 | A1 | 7/2013 | Tseng |
| 2013/0342571 | A1* | 12/2013 | Kinnebrew ............. G06F 3/147 345/633 |
| 2014/0108927 | A1 | 4/2014 | Vaidya et al. |
| 2014/0304665 | A1 | 10/2014 | Holz |
| 2015/0205359 | A1 | 7/2015 | Feng et al. |
| 2015/0347717 | A1 | 12/2015 | Dalal et al. |
| 2016/0371888 | A1 | 12/2016 | Wright et al. |
| 2017/0103672 | A1 | 4/2017 | Dey et al. |
| 2017/0228025 | A1* | 8/2017 | Hall ........................ G06F 3/017 |
| 2018/0088671 | A1 | 3/2018 | Wang |
| 2018/0285062 | A1* | 10/2018 | Ulaganathan ........... G10L 15/07 |
| 2019/0130650 | A1 | 5/2019 | Liu et al. |
| 2020/0306640 | A1* | 10/2020 | Kolen ..................... A63F 13/67 |
| 2020/0366960 | A1 | 11/2020 | Quader et al. |
| 2020/0381021 | A1 | 12/2020 | Rothschild et al. |
| 2020/0393908 | A1 | 12/2020 | Kejariwal |
| 2021/0405763 | A1 | 12/2021 | Liu et al. |
| 2022/0121289 | A1 | 4/2022 | Llamas et al. |
| 2023/0029894 | A1 | 2/2023 | Juenger |
| 2023/0051703 | A1 | 2/2023 | Fortuna |

FOREIGN PATENT DOCUMENTS

| | | |
|---|---|---|
| CN | 115904060 | 4/2023 |
| EP | 4 122 566 | 1/2023 |
| EP | 4 137 916 | 2/2023 |
| JP | 2023/016015 | 2/2023 |
| JP | 2023-021047 | 2/2023 |
| JP | 2023-027017 | 3/2023 |
| KR | 2005-0082559 | 8/2005 |
| WO | WO 2010/001109 | 1/2010 |

OTHER PUBLICATIONS

"Experience and Levels—Ring Fit Adventure Wiki Guide—IGN" May 7, 2020 [Retrieved from the Internet on Dec. 22, 2022] https://www.ign.com/wikis/ring-fit-adventure/Experience_and_Levels.
Miyoshi Maasa et al.; "Ring Fit Adventure" Wikipedia, Aug. 10, 2021 [Retrieved from the Internet on Dec. 20, 2022] https://en.wikipedia.org/w/index.php?title=Ring_Fit_Adventure&oldid=1038055950.
Nintendo of America: "Ring Fit Adventure Overview Trailer—Nintendo Switch" Aug. 31, 2020 [Retrieved from the Internet on Dec. 23, 2022] https://www.youtube.com/watch?v=skBNiJd61Qw.
European Application No. 22183803.0 Extended European Search Report dated Jan. 5, 2023.
European Application No. 22184797.3 Extended European Search Report dated Jan. 10, 2023.
European Application No. 22181663.0 Extended European Search Report dated Nov. 23, 2022.
U.S. Appl. No. 17/390,372 Office Action dated Mar. 2, 2023.
U.S. Appl. No. 17/403,242 Final Office Action dated Apr. 7, 2023.

* cited by examiner

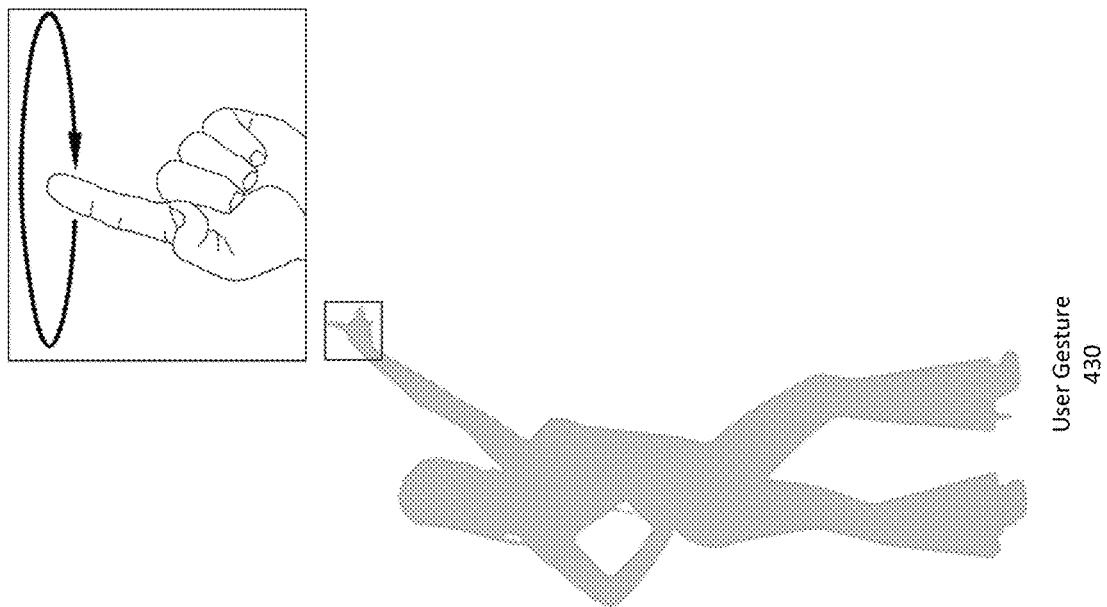
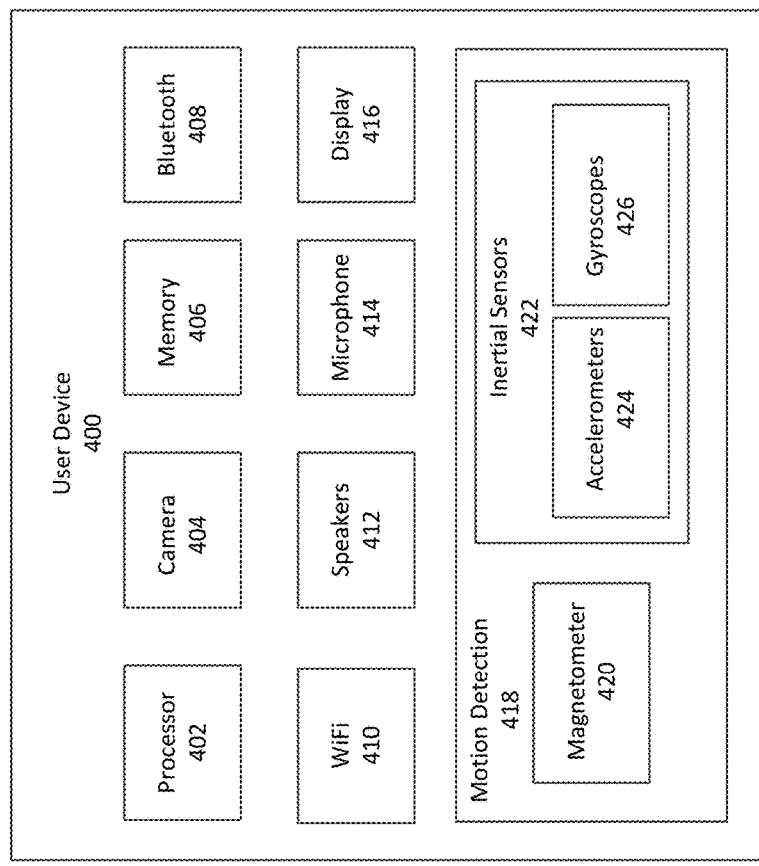
FIG. 4

MOVEMENT-BASED NAVIGATION

CROSS-REFERENCE TO RELATED APPLICATIONS

The present application claims the priority benefit of U.S. patent application 63/223,816 filed Jul. 20, 2021, the disclosure of which is incorporated herein by reference.

BACKGROUND OF THE INVENTION

1. Field of the Invention

The present invention generally relates to movement-based navigation and access. More specifically, the present invention relates to determining navigation and access based on a movement by a user in a virtual environment.

2. Description of the Related Art

Presently available digital content titles support a variety of different scenarios in which players (through their respective avatars or characters) are able to engage in a variety of different types of activities within a virtual environment. Whether playing individually, in teams, and/or against other players, a player playing such content titles may be presented with a rich virtual environment including multiple different locations, levels, and other portions. A player may navigate and interact with such virtual environment (and associated virtual objects, entities, and other player avatars) using controllers or other input devices. Some titles further allow the player (and their friends or other social contacts) to create or otherwise customize user-generated content associated such interactions within the virtual environment.

The player may generally control their respective avatar or character using one or more types of game controllers. There are presently a variety of different controllers (and controller modifications) with different buttons, touchpads, sensors, microphones, etc., in different configurations and layouts. Different combinations of user input (e.g., sequence or synchronization of button presses, touchpad and other gestures, verbal commands, or other input) may be required to perform different types of in-game moves, maneuvers, or other exercise of in-game action. Because different game titles may include different activities, the specific input combinations may result in different in-game moves. In addition, entering an input combination incorrectly may result in a different in-game action than the one intended by the player. Such variety and complexity of game titles, in-game actions, and of controllers represent barriers to entry when players are introduced to a new or unfamiliar game title, controller, or game console system.

There is, therefore, a need in the art for improved systems and methods of determining movement-based navigation and access in virtual environments.

SUMMARY OF THE CLAIMED INVENTION

Embodiments of the present invention include systems and methods for movement-based navigation. A memory of a computing device stores one or more custom actions associated with a pattern of physical movement and a threshold. A navigation server in communication with the computing device receives physical movement data captured by a user device of a user. The navigation server maps the physical movement data to an identified one of the custom actions, wherein the physical movement data matches the associated pattern of physical movement within the associated threshold. The navigation server determines that the user is authorized to access the identified custom action.

BRIEF DESCRIPTION OF THE DRAWINGS

FIG. 4 is a block diagram of an exemplary user device that may be used to perform movement-based navigation.

DETAILED DESCRIPTION

Embodiments of the present invention include systems and methods for movement-based navigation. A memory of a computing device stores one or more custom actions associated with a pattern of physical movement and a threshold. A navigation server in communication with the computing device receives physical movement data captured by a user device of a user. The navigation server maps the physical movement data to an identified one of the custom actions, wherein the physical movement data matches the associated pattern of physical movement within the associated threshold. The navigation server determines that the user is authorized to access the identified custom action.

Figure 1:
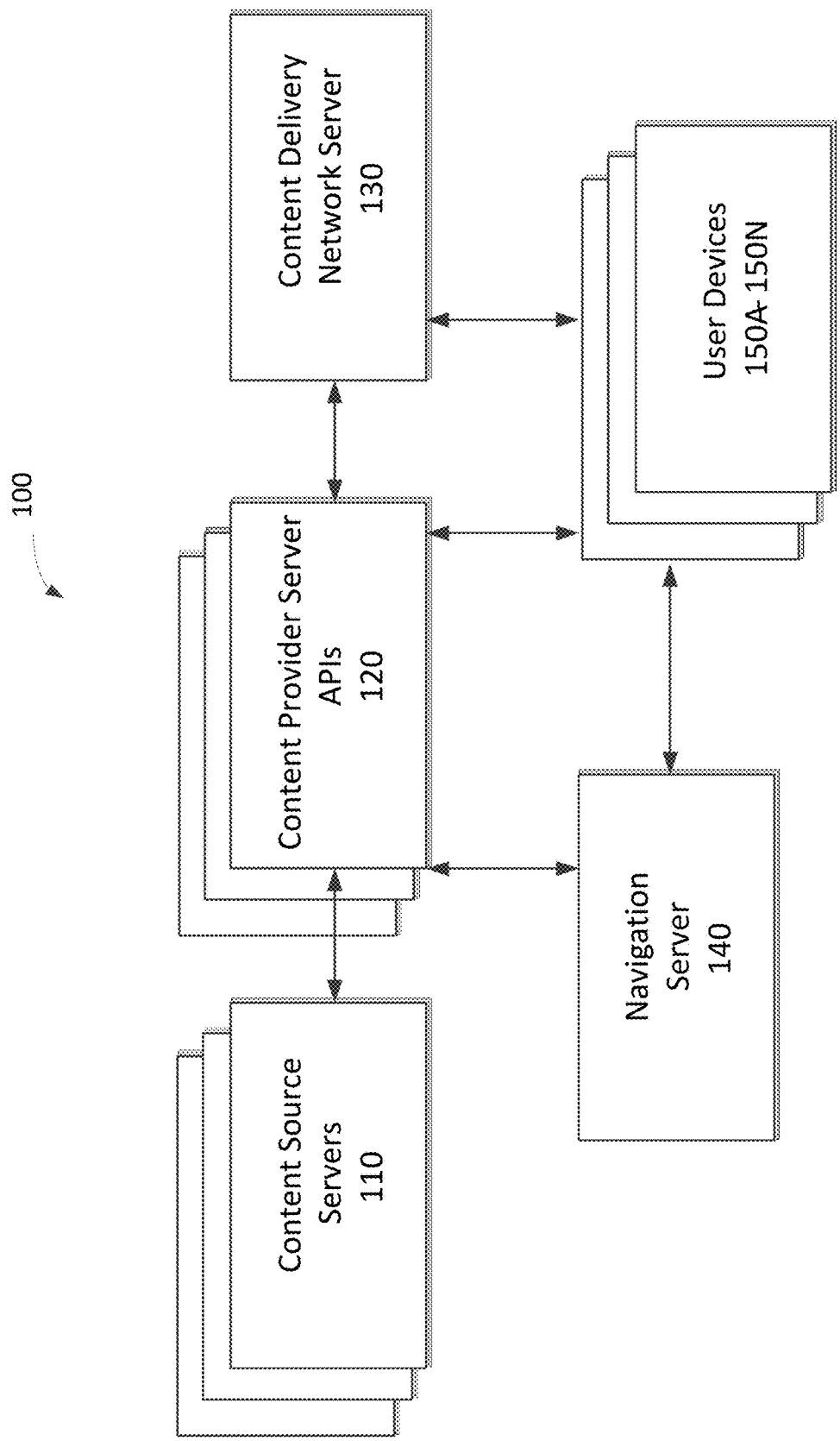
FIG. 1 illustrates an exemplary network environment in which a system for movement-based navigation may be implemented.

FIG. 1 illustrates an exemplary network environment 100 in which a system for sharing movement data may be implemented. The network environment 100 may include one or more content source servers 100 that provide digital content (e.g., games, other applications and services) for distribution, one or more content provider server application program interfaces (APIs) 120, content delivery network server 130, a navigation server 140, and one or more user devices 150A-150N. The servers described herein may include any type of server as is known in the art, including standard hardware computing components such as network and media interfaces, non-transitory computer-readable storage (memory), and processors for executing instructions or accessing information that may be stored in memory. The functionalities of multiple servers may be integrated into a single server. Any of the aforementioned servers (or an integrated server) may take on certain client-side, cache, or proxy server characteristics. These characteristics may depend on the particular network placement of the server or certain configurations of the server.

Content source servers 110 may maintain and provide a variety of digital content available for distribution. The content source servers 110 may be associated with any content provider that makes its content available for access over a communication network. Such content may include not only digital video and games, but also other types of digital applications and services. Such applications and services may include any variety of different digital content and functionalities that may be provided to user devices 150. An example of content source servers 110 may be associated with an Internet website that provides downloadable content and/or streaming content. The content provided by the content source servers 110 can include any type of multimedia content, such as movies, games, static/dynamic content, pictures, social media content, social media websites, etc. The user device 150 may include a plurality of different types of computing devices. In some embodiments, content data is transmitted from the content source servers 110 to a computing device, where the content data is then rendered by the computing device in a format suitable for use by user device 150.

Content source servers 110 may also be inclusive of online servers associated with social media applications, which may be programmed to provide one or more social media graphs the user in order to identify social contacts of the user. These users may not be social contacts or socially associated with the user but may have played one or more video games with the user. The friend listing can include additional information about the user's friends, such as depicting games which are owned by each friend, identifying an online status of the friend (e.g. online, offline, inactive, etc.), the friend's last login and its duration, the last game played by the friend, etc. The social network includes user data, which includes data such as user's social graphs, posts, pictures, videos, biographical information, etc.

The content from content source server 110 may be provided through a content provider server API 120, which allows various types of content sources server 110 to communicate with other servers in the network environment 100 (e.g., user devices 150). The content provider server API 120 may be specific to the particular language, operating system, protocols, etc. of the content source server 110 providing the content, as well as the user devices 150. In a network environment 100 that includes multiple different types of content source servers 110, there may likewise be a corresponding number of content provider server APIs 120 that allow for various formatting, conversion, and other cross-device and cross-platform communication processes for providing content and other services to different user devices 150, which may use different operating systems, protocols, etc., to process such content. As such, applications and services in different formats may be made available so as to be compatible with a variety of different user device 150.

The content provider server API 120 may further facilitate access of each of the user devices 150 to the content hosted or services provided by the content source servers 110, either directly or via content delivery network server 130. Additional information, such as metadata, about the accessed content or service can also be provided by the content provider server API 120 to the user device 150. As described below, the additional information (i.e. metadata) can be usable to provide details about the content or service being provided to the user device 150. In some embodiments, the services provided from the content source servers 110 to the user device 150 via the content provider server API 120 may include supporting services that are associated with other content or services, such as chat services, ratings, and profiles that are associated with a particular game, team, community, etc. In such cases, the content source servers 110 may also communicate with each other via the content provider server API 120.

The content delivery network server 130 may include a server that provides resources, files, etc., related to the content from content source servers 110, including various content and service configurations, to user devices 150. The content delivery network server 130 can also be called upon by the user devices 150 that request to access specific content or services. Content delivery network server 130 may include universe management servers, game servers, streaming media servers, servers hosting downloadable content, and other content delivery servers known in the art.

Navigation server 140 may include any data server known in the art that is capable of receiving data from the user device 150. The content rendered by the navigation server 140 can be for essentially any type of computer application, and may include one or more types of content such as game, movie, audio, images, multimedia, among others. In some embodiments, the content, or portions thereof, is generated by the navigation server 140. In some embodiments, the content, or portions thereof, is streamed from content source server 110 over network 100 to the computing device. In some embodiments, the content, or portions thereof, is streamed from a cloud gaming infrastructure over the network 100 to the computing device. The infrastructure may direct various types of content to be transmitted from the content source servers 110 over the network 100 to the computing device.

In an exemplary embodiment, navigation server 140 may store or access a store that includes a navigation control map for one or more game titles. Each game title may be associated with a different navigation control map, which may include information regarding in-game commands available the respective game title (e.g., commands for accessing certain user-generated content, navigation or transport between locations in the virtual environment), information regarding how the in-game commands correspond to real-world gestures (e.g., custom gestures, gestures selected from a menu). Some game titles may further limit the types of the commands that are available within different levels, activities, or other portions of the associated in-game environment. Such limitations may be saved in activity files generated by UDS systems (described in further detail in relation to FIG. 2) and may further be used to identify which in-game commands may be associated with a specific real-world gestures.

Different real-world gestures-which may be customized by the user—may be associated with different in-game commands. For example, different combinations of verbal, key-based, or gestural commands may indicate that the user wishes to input or initiate a specific in-game command. Such a real-world gesture may be captured and characterized by a camera and/or other sensors (e.g., of the user device(s) 150) to capture images and/or other sensor data regarding the real-world environment in which the user is located. For example, a camera may capture images of the user performing a physical gesture in the real-world. The camera (discussed in further detail in relation to FIG. 4) can be configured to include multiple image capture devices, such as a stereoscopic pair of cameras, an infrared camera, a depth camera, or combinations thereof. In some embodiments, one or more microphones (discussed in further detail in relation to FIG. 4) can also be used to capture sound from the real-world environment of the user. Meanwhile, other sensors (e.g., accelerometers, gyroscopes) associated with the user (e.g., by way of a controller, mobile device, wearable device, handheld device, etc.) may also capture data regarding the real-world gesture.

Such images, audio, and other sensor data my be provided to navigation server 140 for analysis. Using the stored maps, the navigation server 140 may be able to match the received sensor data regarding the real-world gesture (within a predetermined threshold of accuracy) to an in-game command available in the virtual environment of the associated game title. In some implementations, the received sensor data may indicate multiple available in-game commands, and in such cases, different parameters may be used to filter the available in-game commands. As noted above, some game titles allow for different in-game commands to be executed within different portions of the game environment or game sessions. Such data may be provided in activity files and used to filter the available in-game commands and identify which may be available at an identified portion of the game environment or game session currently associated with the user. Alternatively or in addition, a menu regarding the multiple available in-game commands may be displayed in a graphical user interface for selection by the user.

In some embodiments, the user may wish to define custom real-world gestures and link such gestures to specific in-game commands. Using user device 150, the user may add such a customization to a personal navigation map by performing the real-world gesture one or more times to set and calibrate the images or sensor data associated with the real-world gesture. The specific in-game commands may be selected from among the available in-game commands for the virtual environment. Additional parameters or conditions may also be defined, so that the same real-world gesture may have different effects depending on the particular game environment, game title, or other parameters/conditions are presently applicable. For example, the user may define a secret handshake for authenticating accessing private user-generated content or identifying the avatar as associated with the user, a physical signal for sending predefined messages to friends or team members, a gesture for initiating navigation movement within the virtual environment to a designated meeting spot, a dance movement for initiating audio-visual effects, etc.

Thus, the navigation server 140 may map data regarding a real-world gesture to one or more in-game commands and initiate input or otherwise communicate the same to content source server 110, content delivery network server 130, or user device 150. A user who is actively engaging with a virtual environment may therefore provide a custom command by performing a gesture rather than the standard input commands supported by default in the game title. The user may further define the custom commands as being applicable within a variety of different game environments. For example, the user may define a specific real-world gesture as being associated with a command for sending a custom message to a defined group of friend accounts (e.g., "Come join me at [Location]").

The user device 150 may be a server that provides an internal service (e.g., to other servers) in network environment 100. In such cases, user device 150 may correspond to one of the content source servers 110 described herein. Alternatively, the user device 150 may be a client device that may include any number of different gaming consoles, mobile devices, laptops, and desktops. Such user devices 150 may also be configured to access data from other storage media, such as, but not limited to memory cards or disk drives as may be appropriate in the case of downloaded services. Such user devices 150 may include standard hardware computing components such as, but not limited to network and media interfaces, non-transitory computer-readable storage (memory), and processors for executing instructions that may be stored in memory. These user devices 150 may also run using a variety of different operating systems (e.g., iOS, Android), applications or computing languages (e.g., C++, JavaScript). An exemplary client device 150 is described in detail herein with respect to FIG. 5. Each user device 150 may be associated with participants or other types of spectators of a collection of digital content streams.

In some embodiments, the user device 150 is configured to execute games locally on the processing hardware of a computing device or game console. The games or content can be obtained in any form, such as physical media form (e.g., digital discs, tapes, cards, thumb drives, solid state chips or cards, etc.) or by way of download from the Internet, via a communication network. In some embodiments, the computing device functions as a client in communication over the communication network with the cloud gaming infrastructure. The cloud gaming infrastructure may maintain and execute a video game being played by the user device 150. Inputs received from the user device 150, the controller, and the camera (and other sensors), may be transmitted to the cloud gaming infrastructure, which processes the inputs to affect the game state of the executing video game.

Game data from a video game, such as video data, audio data, and tactile feedback data, can be transmitted from the content source servers 110 to the user devices 150. The computer system may further process the game data before transmission to the appropriate device, or may directly transmit the game data to the appropriate device. For example, video and audio streams may be transmitted to the user devices 150.

The user device 150 may also include a module configured to receive inertial sensor data from inertial sensors within the user device 150. The inertial sensor data indicates movement of the user device 150 in accordance with movement of a user by whom the user device 150 is associated with. The movement of the user is based on a virtual reality scene displayed within the user device 150. A route of movement of the user device 150 can be determined from inertial sensor data and a rate of movement of the user device 150. In some embodiments, the route of movement of the head mounted display corresponds to one or more user movements within a set of user movements including a forward lean, a backward lean, a left lean, a right lean, a left head turn, a right head turn, an upward head tilt, a downward head tilt, a squat, and a jump. However, in other embodiments, the route of movement of the head mounted display may correspond to essentially any user movement within the movement capabilities of the human body.

In some embodiments, the user device 150 can be used to manipulate, e.g., grab, move, push, pull, etc., a virtual object in a virtual reality (VR) or an augmented reality (AR) scene, which is displayed on the user device 150 or on another computing device, e.g., a television, a computer, etc. A virtual hand within a game moves when the user moves his/her hand while wearing the user device 150. Moreover, fingers of a virtual hand in the game move when the user moves his/her fingers while wearing the user device 150. Position and/or orientation of the fingers are determined from image data captured using the cameras described above and in FIG. 5 to generate the movement of fingers of the virtual hand.

The display of the user device 150 may generate a three-dimensional scene incorporating an avatar into virtual space or virtual environment with virtual interactive objects. The navigation server 140 receives visual and/or distance information about the user captured by the user device 150. The navigation server 140 extracts movement information describing movement of the user. The movement information can be encoded so as to describe movement of a "skeleton" of the user that is made up of key points within the user's body.

The user's avatar may be automatically transformed from a single digital image into an animated 3D avatar. In particular, the user can upload a digital image or other image on the user device 150 and receive one or more avatars featuring different facial expressions and/or animations in return. The avatar is displayed to the user to be used as any still or animated image (for example, in GIF format). For example, the avatar can be sent to other users via SMS, MMS, e-mail messages, chats (like Facebook chat), instant messengers (like Skype or Windows Messenger), Twitter, blogs, forums or other means of electronic communication in purpose of displaying the user's emotion.

In some embodiments, the avatar may be realistically based on the user, for example having the same facial features, clothing, and body shape. In other embodiments, the avatar may be intentionally unrealistic, for example by mapping the movements of the user to facial features of a celebrity, a movie star, a politician, a video game character, or another user. The avatar may be an amalgam of realistic elements and intentionally unrealistic elements—for example, the face of the user may be used in the avatar, but the avatar may be given different clothing or a different body shape. Alternately, body of the user may be used in the avatar, but the avatar may be given the face of a celebrity, a movie star, a politician, a video game character, or another user.

The user device 150A transmits the information describing movements of the user and/or movements of the corresponding avatar to a second user device 150B or to the navigation server 140 that then sends this information on to the second user device 150, so that the second user device 150B can generate a scene featuring accurate movements by the avatar. The user device 150A receives information describing movements of the second user and/or movements of the corresponding second avatar, from the second user device 150B, or from an intermediary device such as the navigation server 140 that then sends this information on to first user device 150A as it was received from the second user device 150B, so that the first user device 150A can generate a scene featuring accurate movements by the second avatar.

The user device 150 or computing device generates a representation of the movements of the user as captured and has the avatar perform the generated representation of the movements of the user. The user device 150 also generates a representation of the movements of the second user as received and has the second avatar perform the generated representation of the movements of the second user. The user device 150 also updates the virtual space or environment and any virtual interactive objects as appropriate.

When user wishes to access a custom action, such as a locked compartment, or restricted area or portion of a network or electronic storage area or database the user uses their user device 150 to perform physical movement. The navigation server 140 may recognize a pattern of physical movement in a stored set of movements and find the associated custom action and initiates that custom action on the user device 150. In embodiments of the invention, the user device 150 can be set so as always to initiate an additional further custom action in response to the successful detection of a pattern of physical movement. In an embodiment, a reply or acknowledgement signal is generated. For example, the user device 150 could make a sound (such as a short bleep tone) to indicate that it has successfully decoded a rhythm. Another example is that the device could vibrate (using a vibration element, not shown).

Each custom gesture and command may have varying levels of security or thresholds. For example, a more intricate pattern of physical movement may be required permit entry of a high-level custom action, while a less intricate or simpler pattern of physical movement may be required permit entry of a low-level custom action. A simpler pattern may require less steps and movement than an intricate pattern. The security resource 104 could have multiple levels of security for different services. In that case, when the user is granted access to the secured resource and requests a particular service, a security token module of the security system determines whether the user has been granted access to the requested service according to the security tokens provided by the user.

Figure 2:
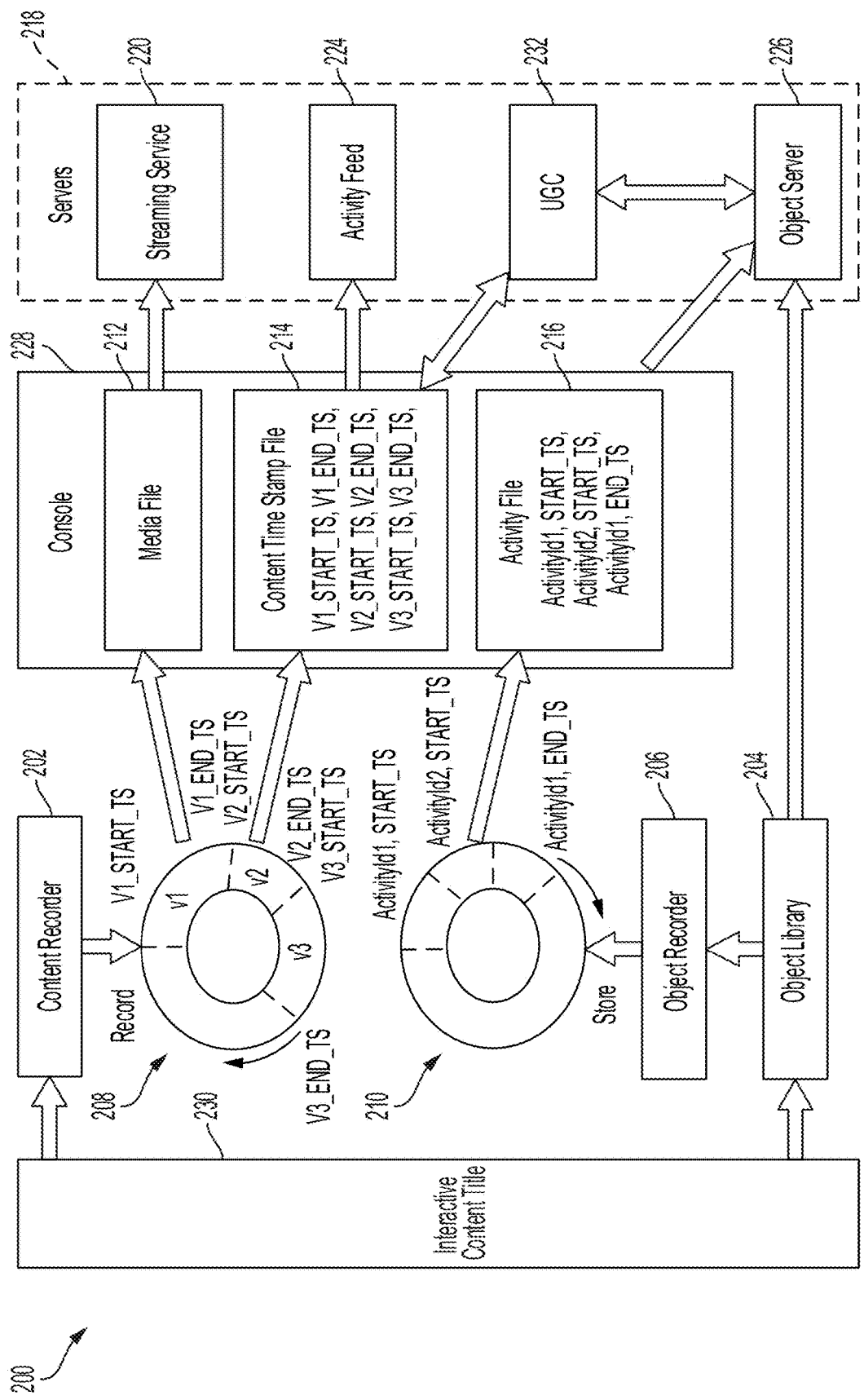
FIG. 2 illustrates an exemplary uniform data system (UDS) that may be used to provide data to a system for movement-based navigation.

FIG. 2 illustrates an exemplary uniform data system (UDS) 200 that may be used to provide data to a system for gesture-based skill search. Based on data provided by UDS, gesture-based search server 140 can be made aware of what in-game objects, entities, activities, and events that users have engaged with, and thus support analysis of and filtering in relation to in-game activities. Each user interaction may be associated the metadata for the type of in-game interaction, location within the in-game environment, and point in time within an in-game timeline, as well as other players, objects, entities, etc., involved. Thus, metadata can be tracked for any of the variety of user interactions that can occur in during a game session, including associated activities, entities, settings, outcomes, actions, effects, locations, and character stats. Such data may further be aggregated, applied to data models, and subject to analytics. Such a UDS data model may be used to assign contextual information to each portion of information in a unified way across games.

As illustrated in FIG. 2, an exemplary console 228 (e.g., a user device 150) and exemplary servers 218 (e.g., streaming server 220, an activity feed server 224, an user-generated content (UGC) server 232, and an object server 226) are shown. In one example, the console 228 may be implemented on or in association with the content source server 110, content delivery network server 130, a cloud server, or on any combination of the servers 218 and servers of FIG. 1. In an exemplary example, a content recorder 202 may receive and record content (e.g., media) from an interactive content title 230 onto a content ring-buffer 208. Such ring-buffer 208 may store multiple content segments (e.g., v1, v2 and v3), start times for each segment (e.g., V1_START_TS, V2_START_TS, V3_START_TS), and end times for each segment (e.g., V1_END_TS, V2_END_TS, V3_END_TS). Such segments may be stored as a media file 212 (e.g., MP4, WebM, etc.) by the console 228. Such media file 212 may be uploaded to the streaming server 220 for storage and subsequent streaming or use, though the media file 212 may be stored on any server, a cloud server, any console 228, or any user device 150. Such start times and end times for each segment may be stored as a content time stamp file 214 by the console 228. Such content time stamp file 214 may also include a streaming ID, which matches a streaming ID of the media file 212, thereby associating the content time stamp file 214 to the media file 212. Such content time stamp file 214 may be uploaded and stored to the activity feed server 224 and/or the UGC server 232, though the content time stamp file 214 may be stored on any server, a cloud server, any console 228, or any user device 150.

Concurrent to the content recorder 202 receiving and recording content from the interactive content title 230, an object library 204 receives data from the interactive content title 230, and an object recorder 206 tracks the data to determine when an object beings and ends. The object library 204 and the object recorder 206 may be implemented on the platform server 120, a cloud server, or on any of the servers 218. When the object recorder 206 detects an object beginning, the object recorder 206 receives object data (e.g., if the object were an activity, user interaction with the activity, activity ID, activity start times, activity end times, activity results, activity types, etc.) from the object library 204 and records the activity data onto an object ring-buffer 210 (e.g., ActivityID1, START_TS; ActivityID2, START_TS; ActivityID3, START_TS). Such activity data recorded onto the object ring-buffer 210 may be stored in the object file 216. Such object file 216 may also include activity start times, activity end times, an activity ID, activity results, activity types (e.g., competitive match, quest, task, etc.), user or peer data related to the activity. For example, an object file 216 may store data regarding an item used during the activity. Such object file 216 may be stored on the object server 226, though the object file 216 may be stored on any server, a cloud server, any console 228, or any user device 130.

Such object data (e.g., the object file 216) may be associated with the content data (e.g., the media file 212 and/or the content time stamp file 214). In one example, the UGC server 232 stores and associates the content time stamp file 214 with the object file 216 based on a match between the streaming ID of the content time stamp file 214 and a corresponding activity ID of the object file 216. In another example, the object server 226 may store the object file 216 and may receive a query from the UGC server 232 for an object file 216. Such query may be executed by searching for an activity ID of an object file 216 that matches a streaming ID of a content time stamp file 214 transmitted with the query. In yet another example, a query of stored content time stamp files 214 may be executed by matching a start time and end time of a content time stamp file 214 with a start time and end time of a corresponding object file 216 transmitted with the query. Such object file 216 may also be associated with the matched content time stamp file 214 by the UGC server 232, though the association may be performed by any server, a cloud server, any console 228, or any user device 150. In another example, an object file 216 and a content time stamp file 214 may be associated by the console 228 during creation of each file 216, 214.

The activity files generated by UDS 200 may be provided or accessed by navigation server 140 for use in analyzing, filtering, and matching data regarding real-world gestures to in-game commands/actions in one or more maps. For example, an activity file may include gameplay data regarding a specific gameplay session of a specific game title by a specific player that is engaged in specific activities at the time the real-world gesture was detected as having been performed. The navigation server 140 may use the data from the activity file to identify the game title, player, in-game activities, and other conditions at the time the real-world gesture was performed. Such identified parameters or conditions under which the real-world gesture is made may be used by navigation server 140 to filter search results for relevance.

Figure 3:
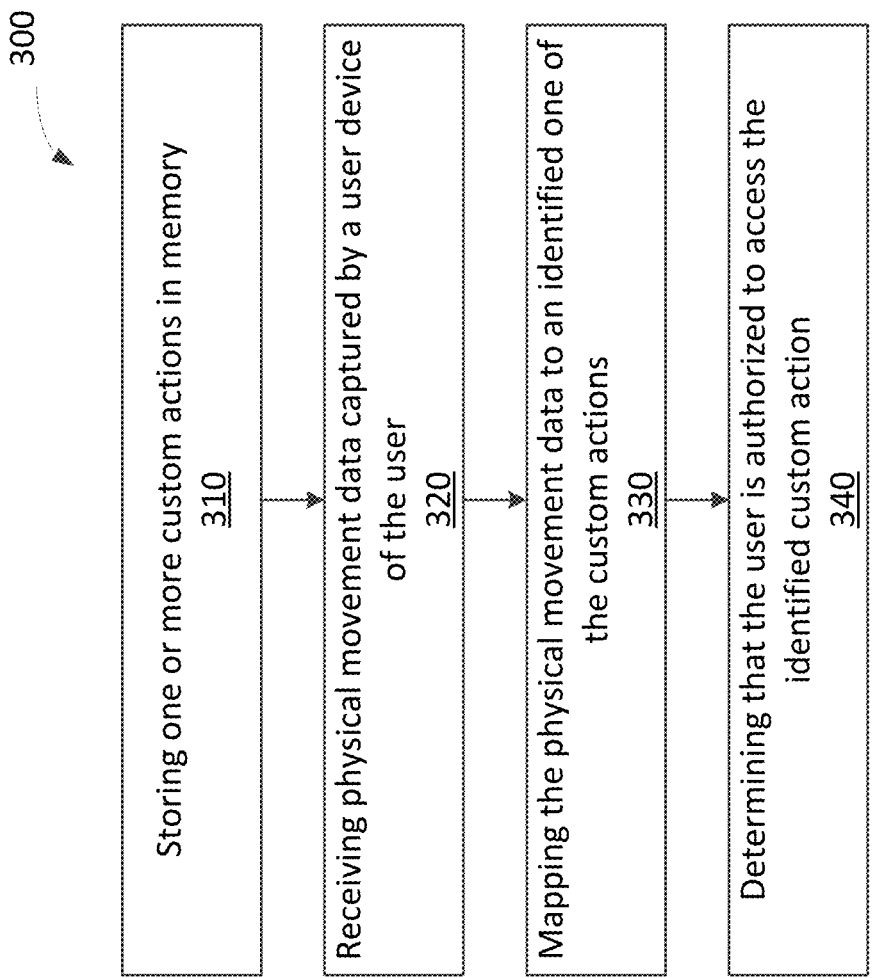
FIG. 3 is a flowchart illustrating an exemplary method for movement-based navigation.

FIG. 3 is a flow chart illustrating an exemplary method for movement-based navigation. The methods 300 of FIG. 3 may be embodied as executable instructions in a non-transitory computer readable storage medium including but not limited to a CD, DVD, or non-volatile memory such as a hard drive. The instructions of the storage medium may be executed by a processor (or processors) to cause various hardware components of a computing device hosting or otherwise accessing the storage medium to effectuate the method. The steps identified in FIG. 3 (and the order thereof) are exemplary and may include various alternatives, equivalents, or derivations thereof including but not limited to the order of execution of the same.

At step 310, one or more custom actions are stored in memory. Each of the custom actions is associated with a pattern of physical movement and a threshold. The threshold corresponds to a level of the custom action. The level of the custom action is determined by the intricacy of the pattern of physical movement.

At step 320, physical movement data captured by a user device of the user is received. At step 330, the physical movement data is mapped to an identified one of the custom actions. The physical movement data matches the associated pattern of physical movement within the associated threshold.

At step 340, it is determined that the user is authorized to access the identified custom action. The user device 150 may then be provided with the access to the identified custom action. In some embodiments, the custom user gesture may be used as an authentication mechanism to lock and unlock content or actions within the virtual environment. For example, the custom gesture may be stored in association with custom conditions (e.g., matching movement metrics within specified thresholds) as a way to control access to personal or shared (team) content or actions. As such, performing the custom gesture correctly (within defined thresholds) may result in execution of a command to unlock the ability to access certain content or action/functions.

In some embodiments, corresponding movement by an avatar associated with the user within a virtual environment may then be rendered based on the physical movement data. One or more other users may be search through one or more social networks associated with the user and the corresponding movement by the avatar may be shared to the one or more other users.

FIG. 4 is a block level diagram of an exemplary user device that may be used to performed a movement-based navigation. It should be understood that more or less components can be included or excluded from the user device 400 than what is shown in FIG. 4, depending on the configuration and functions enabled. The user device 400 may include a processor 402 for executing program instructions. A memory 406 is provided for data storage purposes, and may include both volatile and non-volatile memory. A display 416 is included which provides a visual interface that a user may view. The display 416 can be defined by one single display, or in the form of a separate display screen for each eye. When two display screens are provided, it is possible to provide left-eye and right-eye video content separately. Separate presentation of video content to each eye, for example, can provide for better immersive control of three-dimensional content of the virtual reality scene.

A motion detection module 418 may include any of various kinds of motion sensitive hardware, such as a magnetometer 420, an accelerometer 424, and a gyroscope 426. The user device 400 may be equipped with inertial sensors 422 configured to generate inertial sensor data indicating movement of the user device 400 in accordance with movement of the user with which the user device 400 is associated. The magnetometer 420 measures the strength and direction of the magnetic field in the vicinity of the user device 500. In some embodiments, three magnetometers 420 are used within the user device 400, ensuring an absolute reference for the world-space yaw angle. In some embodiments, the magnetometer 520 is designed to span the Earth's magnetic field, which is ±80 microtesla. Magnetometers are affected by metal, and provide a yaw measurement that is monotonic with actual yaw. The magnetic field may be warped due to metal in the environment, which causes a warp in the yaw measurement. If necessary, this warp can be calibrated using information from other sensors such as the gyroscope or the camera. In some embodiments, the accelerometer 424 is used together with the magnetometer 420 to obtain the inclination and azimuth of the user device 400.

In some embodiments, the present invention can also include one or more external inertial sensors positioned on the body of the user. The present invention may include an operation for comparing the external inertial sensor data to the inertial sensor data received from the inertial sensors 422 in the user device 400 in order to determine a specific movement made by the user.

The accelerometer 424 is a device for measuring acceleration and gravity induced reaction forces. Single and multiple axis (e.g., six-axis) models are able to detect magnitude and direction of the acceleration in different directions. The accelerometer 524 is used to sense inclination, vibration, and shock. In one embodiment, three accelerometers 524 are used to provide the direction of gravity, which gives an absolute reference for two angles (world-space pitch and world-space roll).

The gyroscope 426 is a device for measuring or maintaining orientation, based on the principles of angular momentum. In one embodiment, three gyroscopes 426 provide information about movement across the respective coordinate axes (x, y, and z) based on inertial sensing. The gyroscopes 426 help in detecting fast rotations. However, the gyroscopes 426 can drift overtime without the existence of an absolute reference. This requires resetting the gyroscopes 426 periodically, which can be done using other available information, such as positional/orientation determination based on visual tracking of an object, accelerometer, magnetometer, etc.

A camera 404 is provided for capturing images and image streams of the real-world environment to which the user device 400 is exposed. More than one camera 404 (optionally) may be included in the user device 400, including a camera 404 that is rear-facing (directed away from a user when the user is viewing the display of the user device 400), and a camera 404 that is front-facing (directed towards the user when the user is viewing the display of the user device 400). In some embodiments, a camera 404 may be included in the user device 400 for sensing depth information of objects in the real-world environment to which the user device 500 is exposed.

The user device 400 includes speakers 412 for providing audio output. Also, a microphone 414 may be included for capturing audio from the real-world environment, including sounds from the ambient environment, speech made by the user, etc.

A WiFi module 410 may be included for enabling connection of the user device 400 to the Internet via wireless networking technologies. Also, the user device 400 may include a Bluetooth module 408 for enabling wireless connection to other devices.

It should be understood that the components of the user device 400 as shown in FIG. 4 are examples of components that may be included in user device 400, and do not represent all possible components that can be included in the user device 400. For example, in various embodiments, the user device 400 may or may not include some of the components shown in FIG. 4. In some embodiments, the user device 400 may include additional components not shown in FIG. 4.

In an exemplary embodiment, the user may define a custom real-world user gesture 430 as being associated with a specific in-game command. As illustrated in FIG. 4, the user gesture 430 may be a full-body movement and/or any fine motor skill movement of one or more body parts about which data may be captured by cameras or sensors. Once defined, information regarding the user gesture 430 may be stored in memory and made accessible to navigation server 140 for calibration and matching against later-performed movements and gestures in the real-world environment being monitored by the cameras or sensors.

Navigation server 140 may identify that the user gesture 430 characterized by the sensor data is associated with one or more available in-game commands. The available in-game commands may further be filtered based on one or more activity files associated with the conditions under which the gesture was performed. For example, the gesture may have been performed during a certain gameplay session. Thus, a filtered subset of in-game commands may be identified as being associated with the game title of the gameplay session. Thus, the navigation server 140 may determine that an identified or selected in-game move is mapped to a specific in-game command. The navigation server 140 may thereafter execute the command within the in-game environment, which may result in navigation, access being provided to specific content, inter-player communication, audio-visual effects, etc., available within the associated content title.

Figure 5:
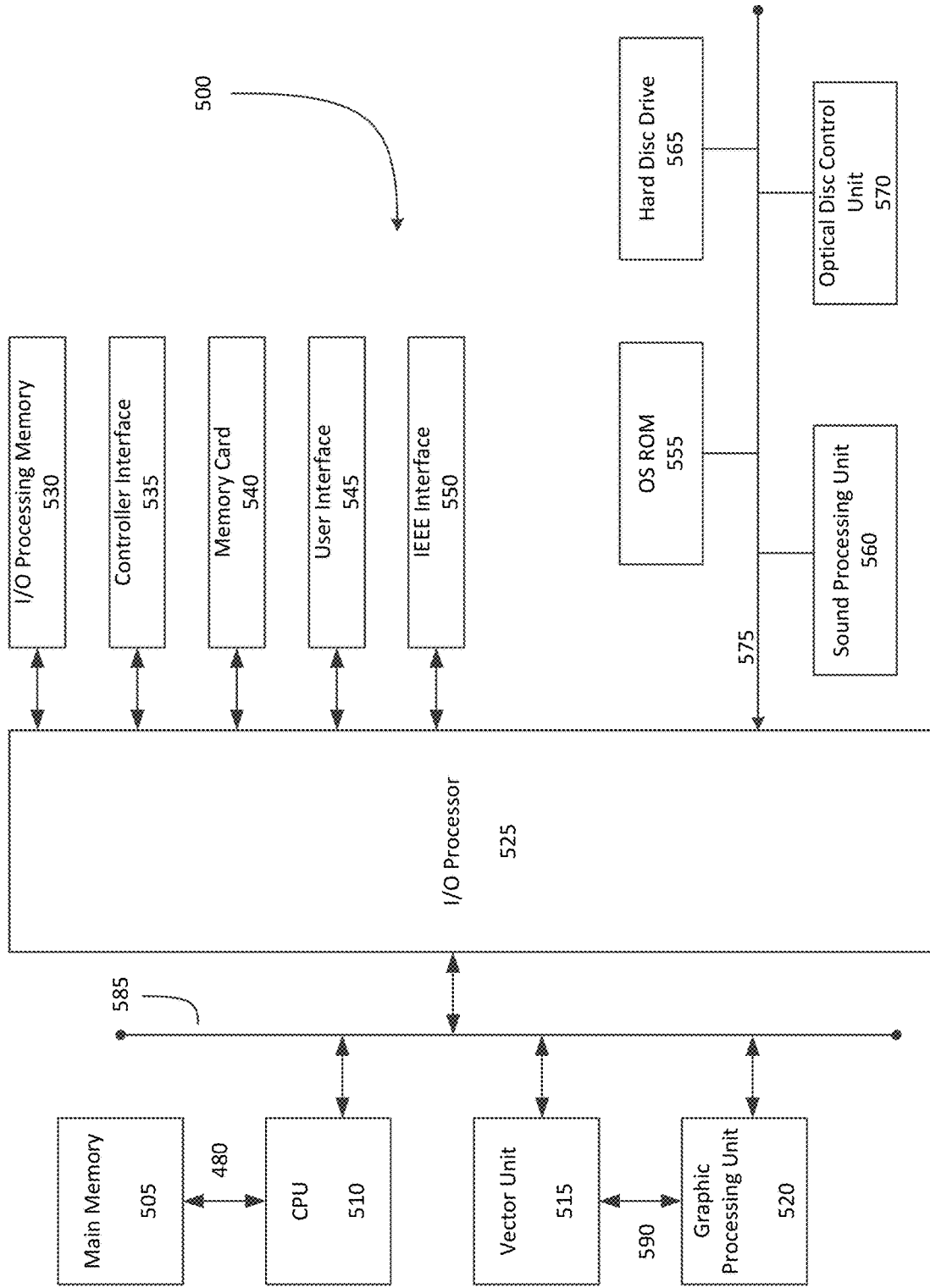
FIG. 5 is a block diagram of an exemplary electronic entertainment system that may be used in embodiments of the present invention.

FIG. 5 is a block diagram of an exemplary electronic entertainment system that may be used in embodiments of the present invention. Entertainment system 500 may be an electronic game console. Alternatively, the entertainment system 500 may be implemented as a general-purpose computer, a set-top box, a hand-held game device, a tablet computing device, or a mobile computing device or phone. Entertainment systems may contain more or less operating components depending on a particular form factor, purpose, or design.

The CPU 510, the vector unit 515, the graphics processing unit 520, and the I/O processor 525 of FIG. 5 communicate via a system bus 585. Further, the CPU 510 of FIG. 5 communicates with the main memory 505 via a dedicated bus 580, while the vector unit 515 and the graphics processing unit 520 may communicate through a dedicated bus 590. The CPU 510 of FIG. 5 executes programs stored in the OS ROM 555 and the main memory 505. The main memory 505 of FIG. 5 may contain pre-stored programs and programs transferred through the I/O Processor 525 from a CD-ROM, DVD-ROM, or other optical disc (not shown) using the optical disc control unit 570. I/O Processor 525 of FIG. 5 may also allow for the introduction of content transferred over a wireless or other communications network (e.g., 4G, LTE, 3G, and so forth). The I/O processor 525 of FIG. 5 primarily controls data exchanges between the various devices of the entertainment system 500 including the CPU 510, the vector unit 515, the graphics processing unit 520, and the controller interface 535.

The graphics processing unit 520 of FIG. 5 executes graphics instructions received from the CPU 510 and the vector unit 515 to produce images for display on a display device (not shown). For example, the vector unit 515 of FIG. 5 may transform objects from three-dimensional coordinates to two-dimensional coordinates, and send the two-dimensional coordinates to the graphics processing unit 520. Furthermore, the sound processing unit 560 executes instructions to produce sound signals that are outputted to an audio device such as speakers (not shown). Other devices may be connected to the entertainment system 500 via the USB interface 545, and the IEEE 1394 interface 550 such as wireless transceivers, which may also be embedded in the system 500 or as a part of some other component such as a processor.

A user of the entertainment system 500 of FIG. 5 provides instructions via the controller interface 535 to the CPU 510. For example, the user may instruct the CPU 510 to store certain game information on the memory card 540 or other non-transitory computer-readable storage media or instruct a character in a game to perform some specified action.

The present invention may be implemented in an application that may be operable by a variety of end user devices. For example, an end user device may be a personal computer, a home entertainment system (e.g., Sony PlayStation2® or Sony PlayStation3® or Sony PlayStation4®), a portable gaming device (e.g., Sony PSP® or Sony Vita®), or a home entertainment system of a different albeit inferior manufacturer. The present methodologies described herein are fully intended to be operable on a variety of devices. The present invention may also be implemented with cross-title neutrality wherein an embodiment of the present system may be utilized across a variety of titles from various publishers.

The present invention may be implemented in an application that may be operable using a variety of devices. Non-transitory computer-readable storage media refer to any medium or media that participate in providing instructions to a central processing unit (CPU) for execution. Such media can take many forms, including, but not limited to, non-volatile and volatile media such as optical or magnetic disks and dynamic memory, respectively. Common forms of non-transitory computer-readable media include, for example, a floppy disk, a flexible disk, a hard disk, magnetic tape, any other magnetic medium, a CD-ROM disk, digital video disk (DVD), any other optical medium, RAM, PROM, EPROM, a FLASHEPROM, and any other memory chip or cartridge.

Various forms of transmission media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU. Various forms of storage may likewise be implemented as well as the necessary network interfaces and network topologies to implement the same.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the claim.

What is claimed is:

1. A method for movement-based navigation, the method comprising:
storing one or more custom actions in memory, wherein each of the custom is associated with a pattern of physical movement corresponding to a set of predetermined metrics and an associated set of thresholds for the set of predetermined metrics;
receiving physical movement data captured by a user device of the user, the physical movement data including a plurality of metrics;
mapping the received metrics of the physical movement data to an identified set of predetermined metrics that correspond to one of the custom actions, wherein the received metrics of the physical movement data matches one or more of the set of predetermined metrics corresponding to the associated pattern of physical movement; and
determining whether the user is authorized to access the identified custom action based on the set of thresholds associated with the matching set of predetermined metrics, wherein the identified custom action is allowed to be performed within a virtual environment currently associated with the user of the user device when the associated thresholds are met, and wherein the identified custom action is restricted from being performed within the virtual environment when at least one of the thresholds in the set is not met.

2. The method of claim 1, further comprising:
initially receiving user input defining a real-world gesture to be associated with the identified custom action, wherein the pattern of physical movement is associated with the real-world gesture defined by the user input; and
analyzing the received user input to identify the corresponding set of predetermined metrics, wherein the corresponding set of predetermined metrics is stored in association with the identified custom action.

3. The method of claim 1, further comprising receiving a request from the user device to share the identified custom action with one or more contacts, and transmitting a notification regarding the identified custom action to user devices associated with the contacts.

4. The method of claim 1, wherein the identified custom action includes navigating an avatar associated with the user to a specified location within the virtual environment.

5. The method of claim 1, wherein the identified custom action includes providing access to specified content within the virtual environment.

6. The method of claim 1, wherein the identified custom action is associated with one or more specified contacts of the user of the user device.

7. The method of claim 1, wherein the identified custom action includes generating a communication within the virtual environment.

8. The method of claim 1, wherein the identified custom action is associated with one or more audio-visual effects within the virtual environment.

9. The method of claim 1, wherein a stored map of the identified custom action is specific to at least one of a game title, set of game titles, game genre, game developer, game console, game controller, set of controller modifications, game environment, and in-game activity.

10. A system for movement-based navigation, the system comprising:
memory that stores one or more custom actions, wherein each of the custom actions is associated with a pattern of physical movement corresponding to a set of predetermined metrics and an associated set of thresholds for the set of predetermined metrics;
a communication interface that receives physical movement data captured by a user device of a user and sent over a communication network, the physical movement data including a plurality of metrics; and
a processor that executes instructions stored in memory, wherein the processor executes the instructions to:
map the received metrics of the physical movement data to an identified set of predetermined metrics that correspond to one of the custom actions, wherein the received metrics of the physical movement data matches one or more of the set of predetermined metrics corresponding to the associated pattern of physical movement, and determine whether the user is authorized to access the identified custom action based on the set of thresholds associated with the matching set of predetermined metrics, wherein the identified custom action is allowed to be performed within a virtual environment currently associated with the user of the user device when the associated thresholds are met, and wherein the identified custom action is restricted from being performed within the virtual environment when at least one of the thresholds in the set is not met.

11. The system of claim 10, wherein the communication interface further initially receives user input defining a real-world gesture to be associated with the identified custom action, wherein the pattern of physical movement is associated with the real-world gesture defined by the user input; and wherein the processor executes further instructions to analyze the received user input to identify the corresponding set of predetermined metrics, wherein the corresponding set of predetermined metrics is stored in association with the identified custom action.

12. The system of claim 10, wherein the communication interface further receives a request from the user device to share the identified custom action with one or more contacts, and transmits a notification regarding the identified custom action to user devices associated with the contacts.

13. The system of claim 10, wherein the identified custom action includes navigating an avatar associated with the user to a specified location within the virtual environment.

14. The system of claim 10, wherein the identified custom action includes providing access to specified content within the virtual environment.

15. The system of claim 10, wherein the identified custom action is associated with one or more specified contacts of the user of the user device.

16. The system of claim 10, wherein the identified custom action includes generating a communication within the virtual environment.

17. The system of claim 10, wherein the identified custom action is associated with one or more audio-visual effects within the virtual environment.

18. The system of claim 10, wherein a stored map of the identified custom action is specific to at least one of a game title, set of game titles, game genre, game developer, game console, game controller, set of controller modifications, game environment, and in-game activity.

19. A non-transitory computer-readable storage medium, having embodied thereon a program executable by a processor to perform a method for movement-based navigation, the method comprising:

storing one or more custom actions in memory, wherein each of the custom is associated with a pattern of physical movement corresponding to a set of predetermined metrics and an associated set of thresholds for the set of predetermined metrics;

receiving physical movement data captured by a user device of the user, the physical movement data including a plurality of metrics;

mapping the received metrics of the physical movement data to an identified set of predetermined metrics that correspond to one of the custom actions, wherein the received metrics of the physical movement data matches one or more of the set of predetermined metrics corresponding to the associated pattern of physical movement; and determining whether the user is authorized to access the identified custom action based on the set of thresholds associated with the matching set of predetermined metrics, wherein the identified custom action is allowed to be performed within a virtual environment currently associated with the user of the user device when the associated thresholds are met, and wherein the identified custom action is restricted from being performed within the virtual environment when at least one of the thresholds in the set is not met.

\* \* \* \* \*